(12) United States Patent
Ukawa et al.

(10) Patent No.: US 11,974,839 B2
(45) Date of Patent: May 7, 2024

(54) CIRCULATORY DYNAMIC MEASURING APPARATUS AND CIRCULATORY DYNAMIC MEASURING METHOD

(71) Applicant: NIHON KOHDEN CORPORATION, Tokyo (JP)

(72) Inventors: Teiji Ukawa, Tokorozawa (JP); Haruka Sato, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 428 days.

(21) Appl. No.: 15/923,040

(22) Filed: Mar. 16, 2018

(65) Prior Publication Data

US 2018/0263503 A1    Sep. 20, 2018

(30) Foreign Application Priority Data

Mar. 16, 2017  (JP) .................. 2017-051476

(51) Int. Cl.
*A61B 5/025* (2006.01)
*A61B 5/02* (2006.01)
*A61B 5/021* (2006.01)
*A61B 5/022* (2006.01)
*A61B 5/0225* (2006.01)
(Continued)

(52) U.S. Cl.
CPC .......... *A61B 5/025* (2013.01); *A61B 5/02028* (2013.01); *A61B 5/02108* (2013.01); *A61B 5/02125* (2013.01); *A61B 5/02225* (2013.01); *A61B 5/0225* (2013.01); *A61B 5/316* (2021.01); *A61B 5/339* (2021.01); *A61B 5/352* (2021.01)

(58) Field of Classification Search
CPC . A61B 5/025; A61B 5/02225; A61B 5/02028; A61B 5/0456; A61B 5/02125; A61B 5/04012; A61B 5/044; A61B 5/02108; A61B 5/0225
See application file for complete search history.

(56) References Cited

U.S. PATENT DOCUMENTS 6,379,309 B1    4/2002  Ogura et al.
8,112,150 B2    2/2012  Naqvi et al.
(Continued)

FOREIGN PATENT DOCUMENTS

JP    H08-131410 A    5/1996
JP    H10-314129 A    12/1998
(Continued)

OTHER PUBLICATIONS

Extended European Search Report issued in Patent Application No. EP 18 16 2208 dated Jun. 25, 2018.
(Continued)

*Primary Examiner* — Yi-Shan Yang
*Assistant Examiner* — Joseph A Tombers
(74) *Attorney, Agent, or Firm* — Pearne & Gordon LLP

(57) ABSTRACT

A circulatory dynamic measuring apparatus includes: an electrocardiogram acquiring section which is configured to acquire an electrocardiogram of a subject; a pulse wave acquiring section which is configured to acquire a poise wave of an upper arm of the subject; and a calculator which is configured to calculate information that relates to a cardiac function of the subject, and that is based on a pulse wave transmit time obtained from the electrocardiogram and the pulse wave.

11 Claims, 11 Drawing Sheets

(51) Int. Cl.
*A61B 5/316* (2021.01)
*A61B 5/339* (2021.01)
*A61B 5/352* (2021.01)

(56) References Cited

U.S. PATENT DOCUMENTS

| | | | |
|---|---|---|---|
| 2002/0026120 A1* | 2/2002 | Ogura | A61B 5/022 600/485 |
| 2007/0004985 A1 | 1/2007 | Suzuki et al. | |
| 2008/0033310 A1* | 2/2008 | Yu | A61B 5/0225 600/493 |
| 2011/0275944 A1 | 11/2011 | Qasem | |
| 2012/0283583 A1* | 11/2012 | Batkin | A61B 5/0225 600/493 |
| 2013/0138000 A1* | 5/2013 | Kinoshita | A61B 5/02225 600/490 |
| 2014/0121544 A1 | 5/2014 | Sugo et al. | |
| 2014/0288445 A1* | 9/2014 | Makkonen | A61B 5/02108 600/490 |
| 2015/0165211 A1 | 6/2015 | Naqvi et al. | |
| 2015/0230706 A1 | 8/2015 | Nakagawa et al. | |
| 2017/0340209 A1* | 11/2017 | Klaassen | A61B 5/11 |
| 2018/0085011 A1* | 3/2018 | Ma | A61B 5/14551 |

FOREIGN PATENT DOCUMENTS

| | | |
|---|---|---|
| JP | 2000-325316 A | 11/2000 |
| JP | 2004-157941 A | 6/2004 |
| JP | 2004-173872 A | 6/2004 |
| JP | 2006-346288 A | 12/2006 |
| JP | 2008-086568 A | 4/2008 |
| JP | 2013-236836 A | 11/2013 |
| JP | 2017-029258 A | 2/2017 |
| WO | 2014-033942 A1 | 3/2014 |

OTHER PUBLICATIONS

Japanese Office Action issued in Japanese Patent Application No. 2017-051476 dated Sep. 15, 2020.
Japanese Opposition for patent application No. 2017-051476 dated Dec. 28, 2021.
Yoshihiro Sugo, et al., "A Non-invasive Continuous Cardiac Output Measurement Method Utilizing ECG and SpO2Pulse Wave", Medical Sciences, vol. 75, No. 2, (2005) , pp. 63-69.
Yoshihiro Sugo, "On Trends and Advancement Status of Non-Invasive Continuous Cardiac Outcome Measurement Techniques Using Electrocardiogram and Sp02 Pulse Wave", Medical Sciences, vol. 83, No. 6, (2013), pp. 527-529.
Documentary evidence dated Dec. 27, 2021.
Japanese Written Opinion for patent application 2017-051476 dated Aug. 4, 2022.
Decision on Opposition for patent application 2017-051476 dated Sep. 27, 2022.
Japanese Notification for Reasons for Revocation for patent application 2017-051476 dated Apr. 22, 2022.
Japanese Notification for Dispatch of Duplicates of a Written Opposition for patent application 2017-051476 dated Feb. 18, 2022.
Japanese Notification of Dispatch of Duplicates a Written Opinion 2017-051476 dated Sep. 27, 2022.
Japanese machine translation of US-20150165211-A1.
Japanese machine translation of US-20110275944-A1.
European Office Action dated Jul. 11, 2023 issued in European Patent Application No. 18 162 208.5.

* cited by examiner

CIRCULATORY DYNAMIC MEASURING APPARATUS AND CIRCULATORY DYNAMIC MEASURING METHOD

CROSS-REFERENCE TO RELATED APPLICATION(S)

This application is based upon and claims the benefit of priority from prior Japanese patent application No. 2017-051476, filed on Mar. 16, 2017, the entire contents of which are incorporated herein by reference.

BACKGROUND

The presently disclosed subject matter relates to a circulatory dynamic measuring apparatus and a circulatory dynamic measuring method.

The PWTT (Pulse Wave Transit Time) is a time period from the apparition of the R wave in an electrocardiogram to that of a puke wave in the periphery. The PWTT is the sum of the PEP (Pre-Ejection Period), the pulse wave transmit time which is in a relatively large blood vessel and which is dependent on the blood pressure, and the pulse wave transmit time which is in a peripheral blood vessel and which is dependent on the vascular resistance.

The PEP indicates the heart contraction function which is one of the cardiac functions, and therefore the PEP is used as an index of heart failure. However, the PWTT contains the pulse wave transmit time dependent on the blood pressure, and the pulse wave transmit time dependent on the vascular resistance. Even when the PWTT is measured, therefore, the measurement value is affected by the blood pressure and the vascular resistance, and hence it is impossible to clearly acquire a change in the PEP.

JP-A-08-131410 discloses a related art in which the blood pressure that is an index of the cardiac functions is measured by measuring the PWTT that correlates with the blood pressure, and determining the blood pressure based on the PWTT.

In the technique, the PWTT is measured based on and echocardiogram, and the fingertip poise wave which is measured by a photoelectric poise wave sensor attached to the fingertip, and the blood pressure is calculated based on the measured PWTT with using pre-acquired correlation between the blood pressure and the PWTT.

In the related art disclosed in JP-A-08-131410, however, the influence of the blood pressure on the PWTT is used. Therefore, the related art is difficult to acquire a change in the PEP contained in the PWTT.

SUMMARY

The presently disclosed subject matter may provide a circulatory dynamic-measuring apparatus and a circulatory dynamic measuring method which can easily measure information relating to the heart contraction function of the subject, simultaneously with a measurement of the blood pressure.

The circulatory dynamic measuring apparatus may comprise: an electrocardiogram acquiring section which is configured to acquire an electrocardiogram of a subject; a pulse wave acquiring section which is configured to acquire a pulse wave of an upper arm of the subject; and a calculator which is configured to calculate information that relates to a cardiac function of the subject, and that is based on a pulse wave transmit time obtained from the electrocardiogram and the pulse wave.

The circulatory dynamic measuring method may comprise: acquiring an electrocardiogram of a subject; acquiring a pulse wave of an upper arm of the subject; and calculating information that relates to a cardiac function of the subject, and that is based on a pulse wave transmit time obtained from the electrocardiogram and the pulse wave which are acquired.

The circulatory dynamic measuring method may comprise: acquiring an electrocardiogram of a subject; acquiring a first pulse wave in a first portion of the subject; acquiring a second pulse wave in a second portion of the subject, the second portion being different from the first portion: calculating a first pulse wave transmit time from the electrocardiogram and the first pulse wave which are acquired; and calculating a second pulse wave transmit time from the electrocardiogram and the second pulse wave which are acquired.

DETAILED DESCRIPTION OF EXEMPLARY EMBODIMENTS

Figure 1:
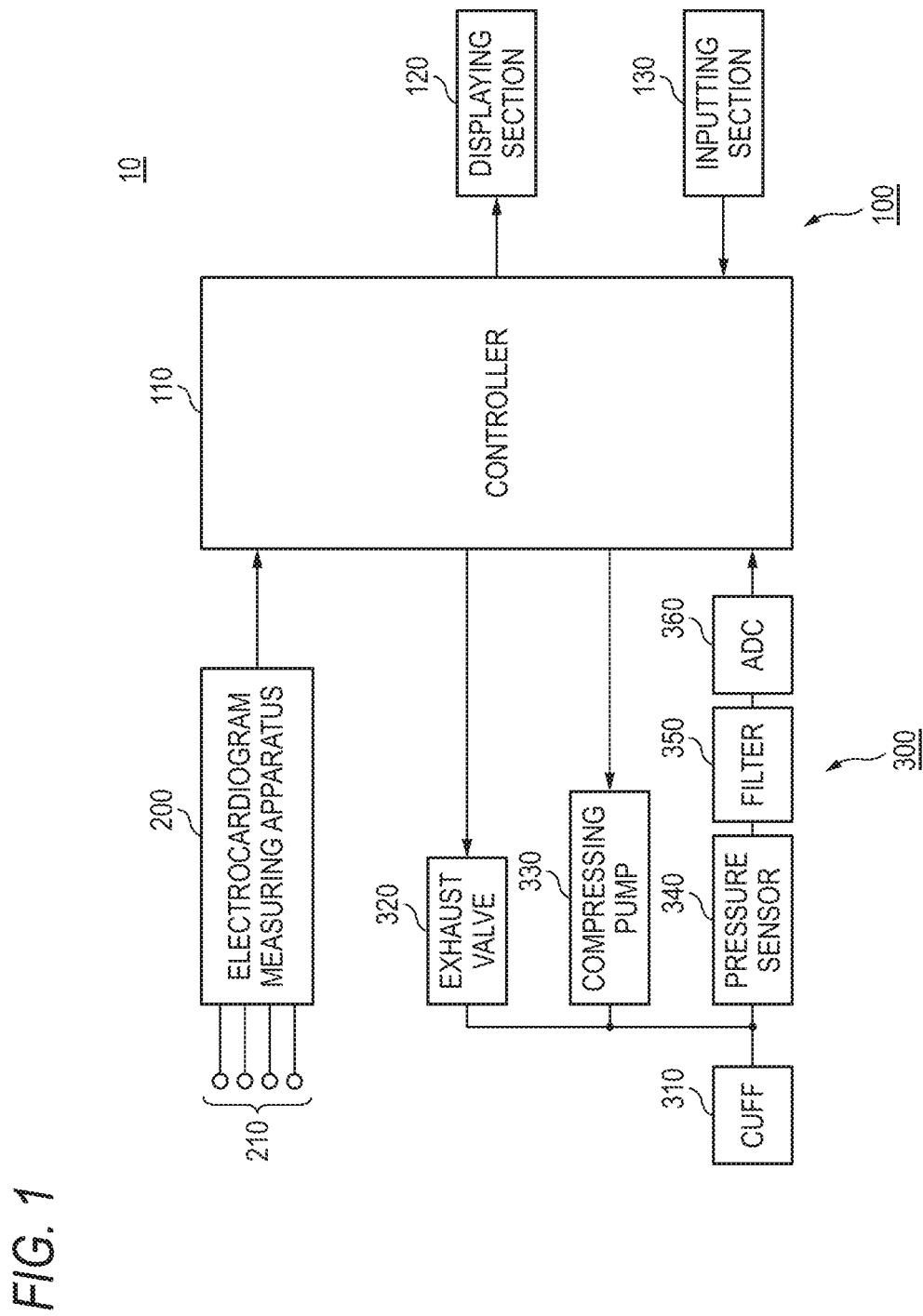
FIG. 1 is a block diagram illustrating the configuration of a circulatory dynamic measuring system of a first embodiment.

Hereinafter, a circulatory dynamic measuring apparatus, circulatory dynamic measuring method, and circulatory dynamic measuring program of an embodiment of the presently disclosed subject matter will be described in detail with reference to the drawings. In the figures, the identical components are denoted by the same reference numerals. In the drawings, the dimension ratios are exaggerated for the sake of convenience in description, and may be sometimes different from the actual ratios.

First Embodiment

FIG. 1 is a block diagram illustrating the configuration of a circulatory dynamic measuring system of a first embodiment. The circulatory dynamic measuring system 10 has an electrocardiogram measuring apparatus 200, a blood pressure measuring apparatus 300, and a circulatory dynamic measuring apparatus 100.

The electrocardiogram measuring apparatus 200 continuously detects an electrocardiogram showing the action potential which is produced by excitation in the myocardium, through a plurality of electrodes 210 attached to predetermined portions of the subject, and transmits the detected electrocardiogram to the circulatory dynamic measuring apparatus 100.

The blood pressure measuring apparatus 300 has a cuff 310, an exhaust valve 320, a compressing pump 330, a pressure sensor 340, a filter 350, and an AD converter 360.

The cuff 310 is attached by wrapping an air bag around the upper arm of the subject. When air is supplied to the air bag of the cuff 310 by the compressing pump 330, the pressure in the air bag (hereinafter, the pressure is referred to as "cuff internal pressure") is increased. This can increase the compression pressure ((hereinafter, referred to as "cuff pressure") which is applied by the cuff 310 to the upper arm of the subject. When the exhaust valve 320 is opened to the atmosphere, the air is gradually exhausted from the cuff 310, and the cuff internal pressure is decreased. As a result, the cuff pressure can be decreased.

The pressure sensor 340 detects the cuff internal pressure. The pulse wave of the subject during processes of increasing and decreasing the cuff pressure is superimposed on the cuff internal pressure. The filter 350 extracts the pulse wave superimposed on the cuff internal pressure, from the detected cuff internal pressure, and outputs the cuff internal pressure and the extracted pulse wave to the AD converter 360 in the form of respective analog signals. The AD converter 360 converts the analog signals of the cuff internal pressure and the pulse wave to digital signal, and transmits the digital signals to the circulatory dynamic measuring apparatus 100.

The circulatory dynamic measuring apparatus 100 has a controller 110, a displaying section 120, and an inputting section 130.

Figure 2:
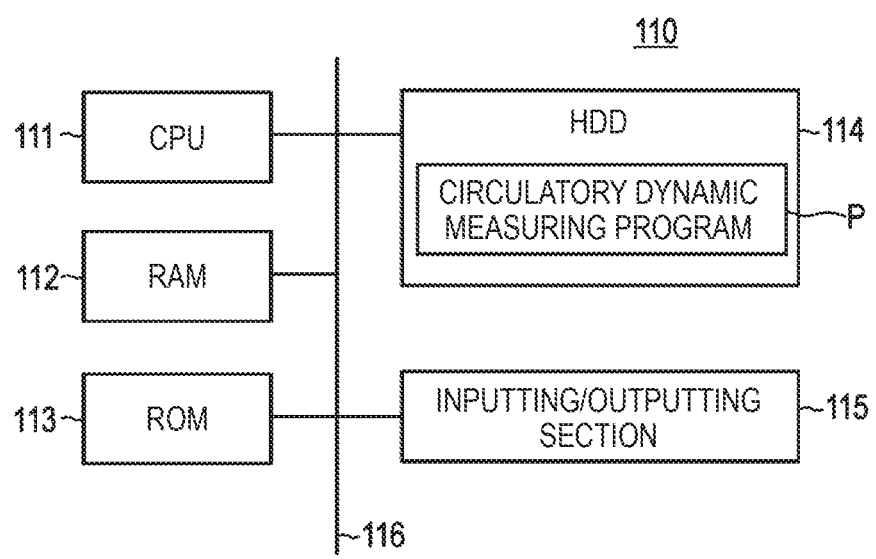
FIG. 2 is a block diagram illustrating the configuration of a controller of a circulatory dynamic measuring apparatus.

FIG. 2 is a block diagram illustrating the configuration of the controller of the circulatory dynamic measuring apparatus.

The controller 110 has a CPU (Central Processing Unit) 111, a RAM (Random Access Memory) 112, a ROM (Read Only Memory) 113, an HHD (Hard Disk Drive) 114, and an inputting/outputting section 115. These components are connected to one another in a mutually communicable manner by a bus 116. The CPU 111 constitutes the electrocardiogram acquiring section, the pulse wave acquiring section, the calculator, and the display image producing section.

In accordance with programs, the CPU 111 controls the components of the controller 110, the displaying section 120, and the inputting section 130, and performs various calculations. The CPU 111 further controls the electrocardiogram measuring apparatus 200 and the blood pressure measuring apparatus 300.

The CPU 111 executes a circulatory dynamic measuring program P stored in the HHD 114 to calculate the pulse wave transit time (hereinafter, referred to as "PWTT") from the electrocardiogram and the pulse wave. Specifically, the CPU 111 performs acquisition of on electrocardiogram by receiving the electrocardiogram from the electrocardiogram measuring apparatus 200. The CPU 111 further receives the cuff internal pressure of the cuff 310 attached to the upper arm of the subject, and the pulse wave (hereinafter, referred to as "cuff pulse wave") of the upper arm which is superimposed on the cuff internal pressure, from the blood pressure measuring apparatus 300, thereby acquiring the cuff Internal pressure and the cuff pulse wave. Then, the CPU 111 calculates the PWTT winch is calculated from the electrocardiogram and the cuff pulse wave (hereinafter, such a PWTT is referred to as "$PWTT_{CF}$"), as information relating to the cardiac functions.

As described later, the $PWTT_{CF}$ particularly reflects the heart contraction function in the cardiac functions. The information relating to the cardiac functions can include information relating to the all cardiac functions is addition to the heart contraction function. The information relating to the cardiac functions includes the $PWTT_{CF}$, a value ($PWTT_{CF}$/ET) which will be described later, and which is obtained by dividing the $PWTT_{CF}$ by the ejection time (hereinafter, referred to as "ET"), and changes over time in these values.

The reason that the $PWTT_{CF}$ reflects the heart contraction function will be described.

Figure 3:
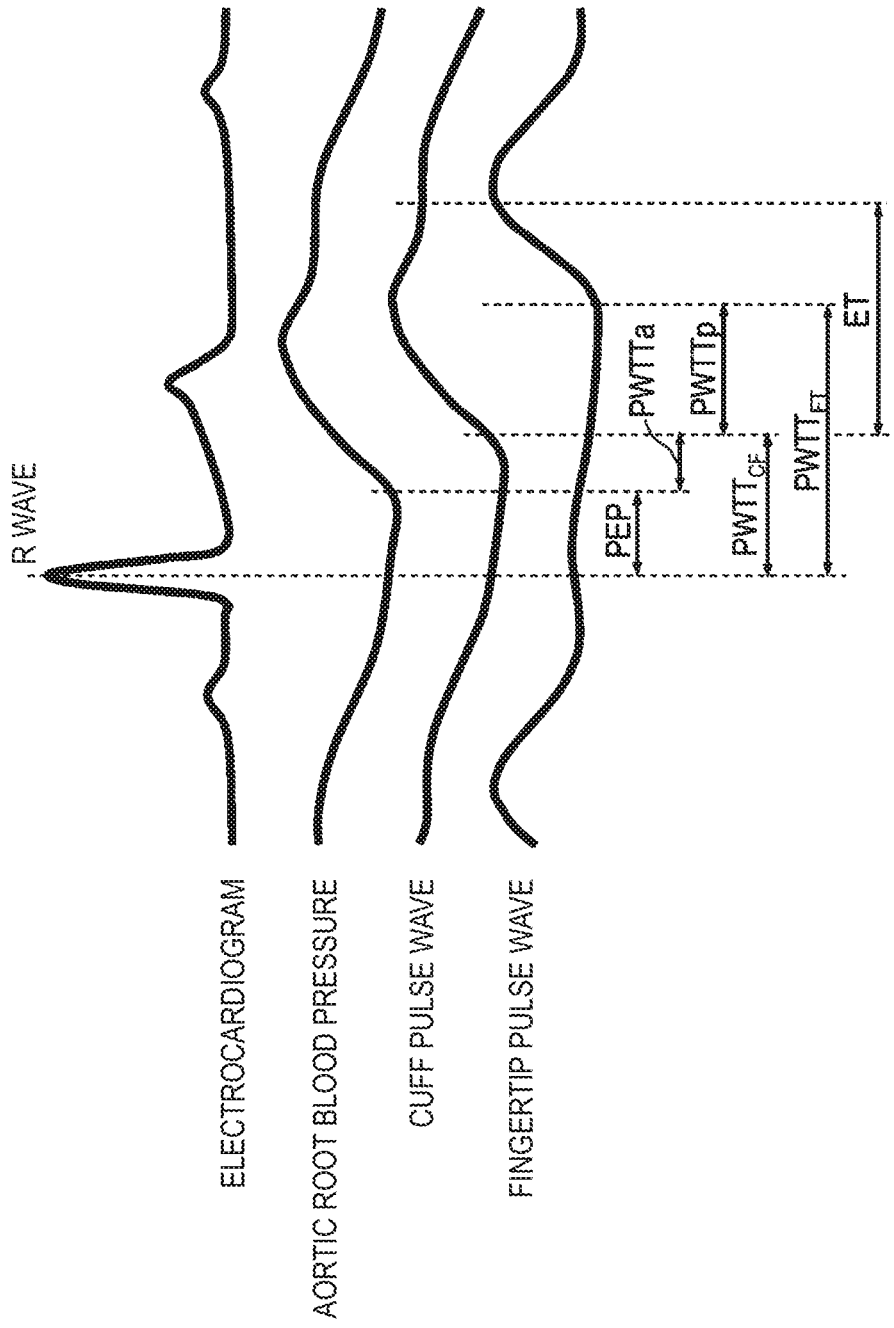
FIG. 3 is a view illustrating an electrocardiogram, the aortic root blood pressure, the cuff pulse wave, and the fingertip pulse wave.

FIG. 3 is a view illustrating the electrocardiogram, the aortic root blood pressure, the cuff pulse wave, and the fingertip pulse wave. The PEP, the PWTT, and the ET will be described with reference to the figure.

The PEP is a time period from the start of the ventricular contraction to the beginning of the actual blood ejection. The PEP appears as the time period from the R wave in the electrocardiogram to the start of rising of the aortic root blood pressure. The PEP reflects the heart contraction function. This is because the left ventricular ejection fraction (hereinafter the ejection fraction is referred to as "EF") which is one of the indexes relating to the contraction function of the left ventricle has a negative correlation with the PEP The EF is a value which is obtained by dividing the amount of blood (ejection amount) which is ejected per beat from the heart, by the left ventricular volume at heart dilatation.

Usually, the aortic root blood pressure is measured by a catheter in which a pressure sensor is disposed in the tip end. Therefore, it is difficult to non-invasively measure the PEP.

The $PWTT_{CF}$ is the time period from the R wave in the electrocardiogram to the start of rising of the cuff pulse wave, and the sum of the PEP and the PWTT that is required for the pulse wave to reach from the heart through the artery to the upper arm to which the cuff is attached (hereinafter, such a PWTT is referred to as "PWTTs"). The $PWTT_{CF}$ can be non-invasively measured based on the electrocardiogram and the cuff pulse wave. The upper arm is a portion which is relatively proximal to the heart. Therefore, the proportion of the $PWTT_a$ in the $PWTT_{CF}$ is relatively small, and by contrast that of the PEP in the $PWTT_{CF}$ is relatively large. Thus, the $PWTT_{CF}$ is relatively less affected by the $PWTT_a$ which is dependent on the blood pressure, and sufficiently reflects the heart contraction function. In place of the PEP, consequently, the $PWTT_{CF}$ can be used as information relating to the cardiac functions.

Also a value (PEP/ET) which is obtained by dividing the PHP by the ET correlates with the EF, and hence reflects the heart contraction function. The ET is a time period from rising of the cuff pulse wave to a notch. As described above, the $PWTT_{CF}$ can be used in place of the PEP. Therefore, also the value ($PWTT_{CF}$/ET) which is obtained by dividing the $PWTT_{CF}$ by the ET can be used in place of the value (PEP/ET) which is obtained by dividing the PEP by the ET. Consequently, the value ($PWTT_{CF}$/ET) which is obtained by dividing the $PWTT_{CF}$ by the FT can be used as information relating to the cardiac functions. The ET can be measured based on the cuff pulse wave.

The PWTT that is required for the pulse wave to reach front the upper arm to which the cuff is attached, through the peripheral artery to the fingertip (hereinafter such a PWTT is referred to as "$PWTT_p$") will be described later in the description of a second embodiment.

The CPU 111 calculates the $PWTT_{CF}$ and the ET based on the cuff pulse wave which is acquired tram the blood pressure measuring apparatus 300. Therefore, the ($PWTT_{CF}$ and the value ($PWTT_{CF}$/ET) which, is obtained by dividing the $PWTT_{CF}$ by the ET can be acquired during the process of measuring the cuff pulse wave while the cuff pressure that is applied to the upper arm of the subject by the cuff 310 attached to the upper arm is changed in order to measure the blood pressure. Namely, the CPU 111 can calculate information relating to the cardiac functions in association with the blood pressure measurement. The $PWTT_{CF}$ can be calculated based on the cuff pulse wave at a time when the cuff pressure is equal to or higher than, the atmospheric pressure.

The CPU 111 may calculate a change over time in the $PWTT_{CF}$ with respect to the PWTT which is calculated from the cuff pulse wave at a predetermined timing, as information relating to the cardiac functions. For example, the timing of hospital discharge can be set as the predetermined tinting. This enables information relating to the cardiac functions to be used as a continuous index of the cardiac functions in a time when the subject is at home.

The CPU 111 can produce a display image in which the calculated information relating to the cardiac functions is displayed, and transmit the display image to the displaying section 120 to cause the image to be displayed thereon.

The CPU 111 can produce a display image in which the acquisition time when the electrocardiogram and the cuff pulse wave are acquired is displayed together with the $PWTT_{CF}$ obtained from the electrocardiogram and cuff pulse wave that are acquired at the acquisition time.

The CPU 111 can produce a display image in which information relating to the cardiac functions is displayed in the form of a two-dimensional graph in which the acquisition time when the electrocardiogram and the cuff pulse wave are acquired is set as the abscissa, and the $PWTT_{CF}$ that is obtained from the electrocardiogram and cuff pulse wave that are acquired at the acquisition time of the abscissa is set as the ordinate.

The CPU 111 performs, on the blood pressure measuring apparatus 300, a control in which the cuff internal pressure is changed based on the cuff internal pressure and cuff pulse wave that are received from the blood pressure measuring apparatus 300. Specifically, the CPU 111 performs, on the blood pressure measuring apparatus 300, a control in which, in order to conduct the blood pressure measurement by the oscillometric method, the cuff internal pressure is increased until the pressure reaches a predetermined value, and then decreases the pressure. The CPU 111 calculates the systolic blood pressure, the diastolic blood pressure, and the mean blood pressure based on the cuff internal pressure and amplitude of the cuff pulse wave which change during the process of increasing and decreasing the cuff internal pressure.

A correspondence table of a control signal for changing the cuff internal pressure, and the cuff internal pressure may be previously stored in the HHD 114, and, with reference to the correspondence table, the cuff internal pressure may be calculated based on the control signal. In this case, the CPU 111 is not required to receive the cuff internal pressure from the blood pressure measuring apparatus 300.

The CPU 111 can produce a display image in which at least one of the calculated systolic, diastolic, and mean blood pressures, and information relating to the cardiac functions are displayed in correlation with each other.

Figure 4:
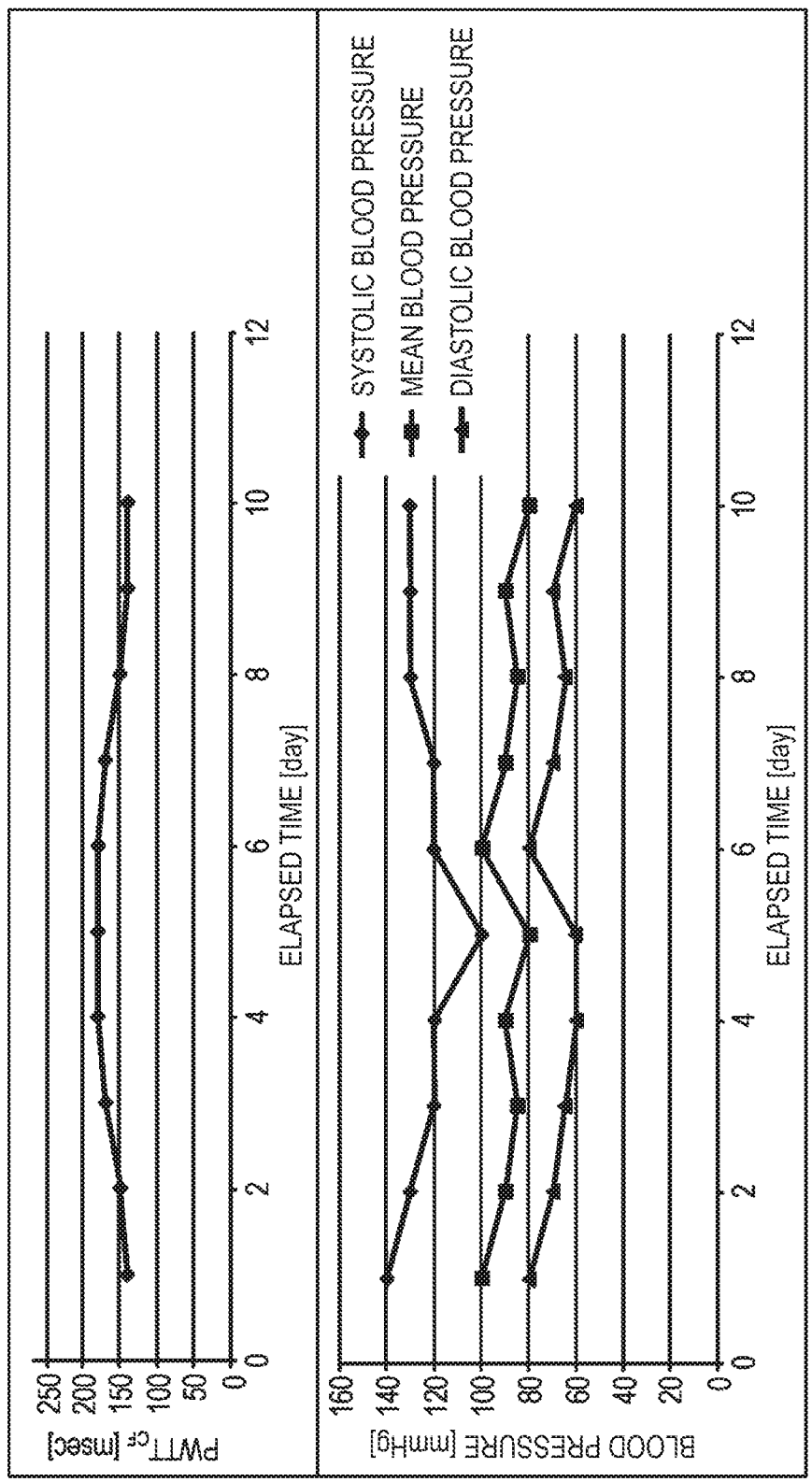
FIG. 4 is a view illustrating an example of a display image in which the $PWTT_{CF}$ that is calculated from an electrocardiogram and the cuff pulse wave, and the systolic blood pressure, the diastolic blood pressure, and the mean blood pressure are simultaneously displayed.

FIG. 4 is a view illustrating an example of the display image in which the $PWTT_{CF}$, and the systolic blood pressure, the diastolic blood pressure, and the mean blood pressure are simultaneously displayed.

The display image of FIG. 4 is configured by two-dimensional graphs of time transitions of the $PWTT_{CF}$ which is information relating to the cardiac functions, and those of the systolic blood pressure, the diastolic blood pressure, and the mean blood pressure, and shows changes over time in these values. The abscissa indicates the elapsed time from the timing of hospital discharge of the subject. In the display image, the span and scale of the elapsed time of the abscissa are common in the two-dimensional graph of the $PWTT_{CF}$, and that of the time transitions of the systolic blood pressure, the diastolic blood pressure, and the mean blood pressure. Therefore, the $PWTT_{CF}$ and the systolic blood pressure, the diastolic blood pressure, and the mean blood pressure are displayed in correlation with each other. The blood pressure which is a usual index of circulatory dynamics including the cardiac functions is displayed together with the $PWTT_{CF}$ reflecting the heart contraction function, thereby enabling a sign of heart failure to be early detected.

Although, in the display image shown in FIG. 4, the abscissa indicates the elapsed time from the timing of hospital discharge of the subject, the abscissa may indicate the acquisition time when the electrocardiogram and the cuff pulse wave are acquired. The acquisition time may be the year, month, date, and time (hour and minute) when, the electrocardiogram and the cuff pulse wave are acquired. In this case, the ordinates may indicate the $PWTT_{CF}$ which is obtained of the electrocardiogram and cuff pulse wave that are acquired at the acquisition time of the abscissa, and the systolic blood pressure, the diastolic blood pressure, and the mean blood pressure. The acquisition time may be additionally indicated at each plot of the two-dimensional graphs shown in FIG. 4.

The CPU 111 outputs the information relating to the cardiac functions of the subject, and the display image to the displaying section 120 through the inputting/outputting section 115.

The RAM 112 is a volatile storage device, and temporarily stores programs and various data including measurement data.

The ROM 113 is a non-volatile storage device, and stores a wide variety of data including various set data which are used when the circulatory dynamic measuring program P is executed.

The HHD 114 stores various programs including the operating system and the circulatory dynamic measuring program P, and a wide variety of data including measurement data and baste information of the subject. The basic information of the subject can include the ID, name, and age of the subject.

The inputting/outputting section 115 is an interlace for exchanging signals between the displaying section 120 and the inputting section 130. The inputting/outputting section 115 can be configured by, for example, an interface board. The inputting/outputting section 115 constitutes the information outputting section and the image outputting section.

The displaying section 120 displays the information relating to the cardiac functions of the subject, and display image which are received from the controller 110. The displaying section 120 can be configured by a liquid crystal display or the like.

The inputting section 130 receives various inputs. For example, the various inputs include the basic information of the subject. The inputting section 130 can be configured by a keyboard, a touch panel, or dedicated keys.

Figure 5:
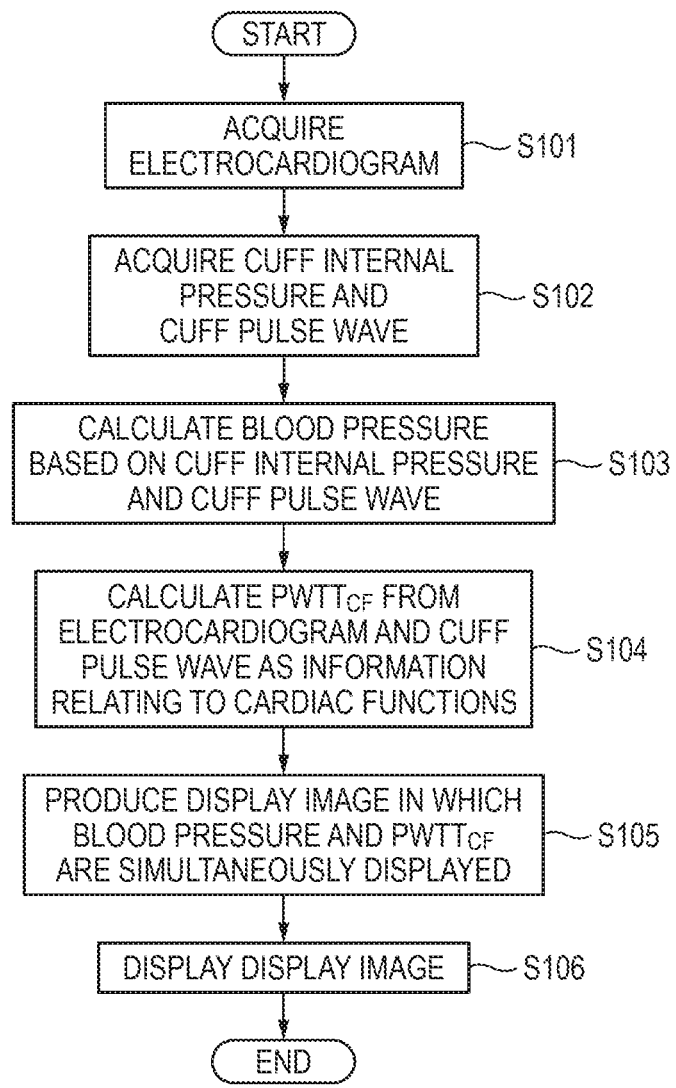
FIG. 5 is a flowchart illustrating the operation of the circulatory dynamic measuring apparatus.

FIG. 5 is a flowchart illustrating the operation of the circulatory dynamic measuring apparatus. The flowchart can be executed by the CPU 111 in accordance with the circulatory dynamic measuring program P.

The CPU 111 acquires the electrocardiogram of the subject from the electrocardiogram measuring apparatus 200 (S101).

The CPU 111 acquires the cuff internal pressure and the cuff pulse wave Horn the blood pressure measuring apparatus 300 (S102).

The CPU 111 calculates the blood pressure based on the cuff internal pressure and the cuff pulse wave (S103).

The CPU 111 calculates the $PWTT_{CF}$ from the electrocardiogram and the cuff pulse wave as information relating to the cardiac functions (S104).

The CPU 111 produces a display image in which the blood pressure and the $PWTT_{CF}$ are simultaneously displayed (S105).

The CPU 111 transmits the display image to the displaying section 120 to cause the image to be displayed thereon (S106).

The embodiment attains the following effects.

The information that is based on the pulse wave transmit time which is obtained from the electrocardiogram and the pulse wave of the upper arm, and that relates to the cardiac functions of the subject is calculated. Therefore, the information relating to the heart contracttion function of the subject can be easily measured simultaneously with the measurement of the blood pressure.

Moreover, a pulse wave which is superimposed on the cuff internal pressure is acquired as the pulse wave of the upper arm of the subject in the state where a pressure that is equal to or higher than the atmospheric pressure is applied to the upper arm by the cuff attached to the upper arm. Therefore, the information relating to foe heart contraction function can be measured by using the pulse wave of the upper arm which is measured in the blood pressure measurement performed by the cuff.

Moreover, the pulse wave of the upper arm of the subject is acquired during the process of changing the cuff pressure which is applied to the upper arm by the cuff attached to the upper arm, in order to measure the blood pressure. The cuff pressure applied to the upper arm by the cuff may be high pressure, low pressure, arbitrary pressure or combination including at least two of them. Therefore, the information relating to the heart contraction function can be measured during the process of measuring the blood pressure.

Moreover, a change over time in the pulse wave transmit time with respect to that which is calculated from the pulse wave at a predetermined timing is calculated as the information relating to the cardiac functions. At a time, for example, when the subject is at home, therefore, a change can be easily sensed from the heart contraction function which was normal at the timing of hospital discharge, and hence a sign of heart failure ears be early detected.

Moreover, a display image is produced in winch the acquisition time when the electrocardiogram and the pulse wave are acquired is displayed together with the information that relates to the cardiac functions of the subject, and that is based on the pulse wave transmit time obtained from the electrocardiogram and pulse wave that are acquired at the acquisition time. Therefore, the date and time corresponding to the information relating to the cardiac functions of the subject can be easily known.

Moreover, a display image is produced in which the information relating to the cardiac functions of the subject is displayed in the form of a two-dimensional graph in which the acquisition time when the electrocardiogram and the cuff pulse wave are acquired is set as the abscissa, and the information that relates to the cardiac functions of the subject, and that is based on the pulse wave transmit time obtained from the electrocardiogram and pulse wave which are acquired at the acquisition time is set as the ordinate. Therefore, the change over time in the information relating to the cardiac functions of the subject can be clearly known as time transition.

Moreover, a display image in which the information relating to the cardiac functions and the blood pressure are displayed in correlation with each other is produced. Therefore, the blood pressure which is a usual index of circulatory dynamics is displayed together with the information reflecting the heart contraction function, thereby enabling a sign of heart failure to be detected accurately and early.

Moreover, the apparatus has the information outputting section which outputs the information relating to the cardiac functions of the subject. Therefore, the information relating to the cardiac functions of the subject can be transmitted as data.

Moreover, the apparatus has the image outputting section which outputs the above-described display image. Therefore, the display image can be transmitted as data.

Second Embodiment

The second embodiment will be described. The embodiment is different from the first embodiment in the following points. In the embodiment, a first pulse wave transmit time is calculated based on an electrocardiogram of the subject, and a first pulse wave in a predetermined first portion, and a second pulse wave transmit time is calculated based on the electrocardiogram, and a second pulse wave in a second portion which is different from the first portion. A display image in which the first and second pulse wave transmit times are simultaneously displayed is produced. In the description of the embodiment, description which is duplicated with that of the first embodiment will be omitted or simplified.

Figure 6:
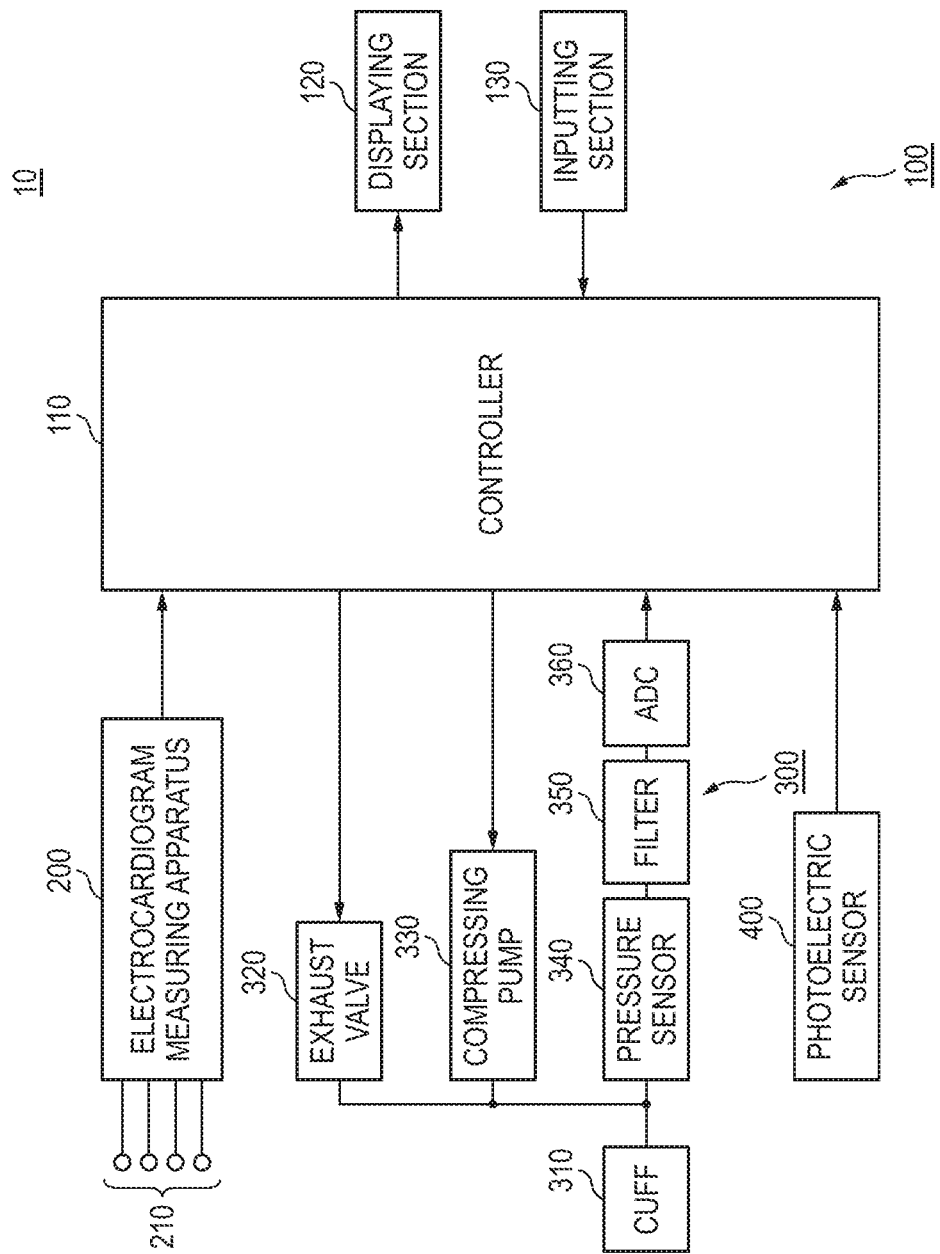
FIG. 6 is a block diagram illustrating the configuration of a circulatory dynamic measuring system of a second embodiment.

FIG. 6 is a block diagram illustrating the configuration of a circulatory dynamic measuring system of the embodiment. The circulatory dynamic measuring system 10 has the electrocardiogram measuring apparatus 200, the blood pressure measuring apparatus 300, a photoelectric sensor 400, and the circulatory dynamic measuring apparatus 100.

The electrocardiogram measuring apparatus 200 transmits the detected electrocardiogram of the subject to the circulatory dynamic measuring apparatus 100.

The blood pressure measuring apparatus 300 transmits the cuff internal pressure and cuff pulse wave which are measured during the process of changing the cuff pressure of the cuff 310 attached to the upper arm of the subject to the circulatory dynamic measuring apparatus 100. The upper arm of the subject can constitute the first portion. The cuff pulse wave can constitute the first pulse wave.

The photoelectric sensor 400 is attached to, for example, the fingertip of the subject, measures the oxygen saturation ($SpO_2$) in the blood, and transmits the fingertip pulse wave which is the pulse wave in the fingertip, to the circulatory dynamic measuring apparatus 100. The fingertip of the subject can constitute the second portion. The fingertip pulse wave can constitute the second pulse wave.

The first portion is requested to be different from the second portion, and may be, for example, the wrist. For example, the second portion can be the ankle which is more distal from the heart than the first portion. In this case, the second pulse wave can be measured by a cuff attached to the ankle.

The circulatory dynamic measuring apparatus 100 has the controller 150, the displaying section 120, and the inputting section 130.

The configuration of the controller 110 is similar to that in the first embodiment, and shown in FIG. 2.

The controller 110 has the CPU 111, the RAM 112, the ROM 113, and the HHD 114. The CPU 111 constitutes the electrocardiogram acquiring section, the first pulse wave acquiring section, the second pulse wave acquiring section, the first calculator, the second calculator, the third calculator, the fourth calculator, the display image producing section, and the blood pressure calculator.

The CPU 111 calculates the $PWTT_{CF}$ from the electrocardiogram and the cuff pulse wave. Specifically, the CPU 111 receives the electrocardiogram from the electrocardiogram measuring apparatus 200 to acquire the electrocardiogram. The CPU 111 receives the cuff internal pressure of the cuff 310 attached to the upper arm of the subject, and the cuff pulse wave superimposed on the cuff internal pressure, from the blood pressure measuring apparatus 300, thereby acquiring the cuff internal pressure and the cuff pulse wave. Then the CPU 111 calculates the $PWTT_{CF}$ from the electrocardiogram and cuff pulse wave which are acquired. The $PWTT_{CF}$ constitutes the first pulse wave transmit time.

The CPU 111 calculates, from the electrocardiogram and the fingertip pulse wave, the PWTT in the period required for the pulse wave to reach from the heart through the artery to the fingertip to which the photoelectric sensor 400 is attached (hereinafter, such PWTT is referred to as "$PWTT_{FT}$"). Specifically, the CPU 111 receives the fingertip pulse wave from the photoelectric sensor 400 to acquire the fingertip pulse wave, and calculates the $PWTT_{FT}$ from the electrocardiogram and the fingertip pulse wave. The $PWTT_{FT}$ constitutes the second pulse wave transmit time.

Referring again to FIG. 3, the relationship between the $PWTT_{CF}$ and the $PWTT_{FT}$ will be described.

As described above, the $PWTT_{CF}$ is the time period from the R wave in the electrocardiogram to the start of rising of the cuff pulse wave, and is the sum of the PEP and the $PWTT_a$. The $PWTT_{FT}$ is the time period from the R wave in the electrocardiogram to the start of rising of the fingertip pulse wave, and is the sum of the PEP, the $PWTT_a$, and the $PWTT_p$. The $PWTT_p$ is the difference ($PWTT_{FT}-PWTT_{CF}$) between the $PWTT_{CF}$ and the $PWTT_{FT}$. When the $PWTT_p$, and the $PWTT_{FT}$ are compared with each other, the $PWTT_{FT}$ contains the $PWTT_p$, and by contrast the $PWTT_{CF}$ does not contain the $PWTT_p$. The $PWTT_p$ the PWTT that is required for the pulse wave to reach from the upper arm to which the cuff is attached, through the peripheral artery to the fingertip, and reflects the vascular resistance. Therefore, the state of the vascular resistance can be known by comparing the $PWTT_{CF}$ with the $PWTT_{FT}$ with each other. On the other hand, the $PWTT_{CF}$ does not contain the $PWTT_p$, and hence the proportion of the PEP in the $PWTT_{CF}$ is larger than that of the PEP in the $PWTT_{FT}$. As described above, the PEP reflects the heart contraction function. When the $PWTT_{CF}$ and the $PWTT_{FT}$ are compared with each other, therefore, also the state of the heart contraction function can be known.

The CPU 111 calculates the difference (i.e., the $PWTT_p$) between the $PWTT_{CF}$ and the $PWTT_{FT}$. Also, the CPU 111 calculates a two-dimensional graph of the relationship between any two of the $PWTT_{CF}$, the $PWTT_{FT}$, and the difference between the $PWTT_{CF}$ and the $PWTT_{FT}$.

The CPU 111 calculates the blood pressure based on the cuff internal pressure and the cuff pulse wave.

The CPU 111 produces a display image from which the slates of of the heart contraction function and the vascular resistance can be simultaneously known.

The display image can be an image in which the two-dimensional graph of the relationship between any two of the $PWTT_{CF}$, the $PWTT_{FT}$, and the difference between the $PWTT_{CF}$ and the $PWTT_{FT}$ is displayed.

The display intake can be an image in which any two of the $PWTT_{CF}$, the $PWTT_{FT}$, and the difference between the $PWTT_{CF}$ and the $PWTT_{FT}$ are simultaneously displayed. In the display image, the acquisition time when the electrocardiogram, the cuff pulse wave, and the fingertip pulse wave are acquired can be further displayed. Namely, any two of the $PWTT_{CF}$ which is calculated from the electrocardiogram and cuff pulse wave that are acquired at the acquisition time, the $PWTT_{FT}$ which is calculated from the electrocardiogram and fingertip pulse wave that are acquired at the acquisition time, and the difference between the two values can be displayed together with the acquisition time.

The display image can be two-dimensional graphs in which the acquisition time is set as the abscissa, and any two of the $PWTT_{CF}$ which is calculated from the electrocardiogram and cuff pulse wave that are acquired at the acquisition time of the abscissa, the $PWTT_{FT}$ which is calculated from the electrocardiogram and the fingertip pulse wave, and the difference between the two values are set as the ordinates.

The display image can be an image in which any two of the $PWTT_{CF}$, the $PWTT_{FT}$, and the difference between the $PWTT_{CF}$ and the $PWTT_{FT}$ are displayed in correlation with the blood pressure. The display image ears be an image in which the two-dimensional graph of the relationship between any two of the $PWTT_{CF}$, the $PWTT_{FT}$, and the difference between the $PWTT_{CF}$ and the $PWTT_{FT}$ is displayed simultaneously with the blood pressure.

The display image can further contain the value ($PWTT_{CF}$/ET) which is obtained by dividing the $PWTT_{CF}$ by the EX.

The CPU 111 may output: at least two of the $PWTT_{CF}$, the $PWTT_{FT}$, and the difference between the $PWTT_{CF}$ and the $PWTT_{FT}$; the value which is obtained by dividing the $PWTT_{CF}$ by the ET; the blood pressure; and the display image, to the displaying section 120 through the inputting/outputting section 115, and cause these sets of information to be displayed thereon.

Figure 7:
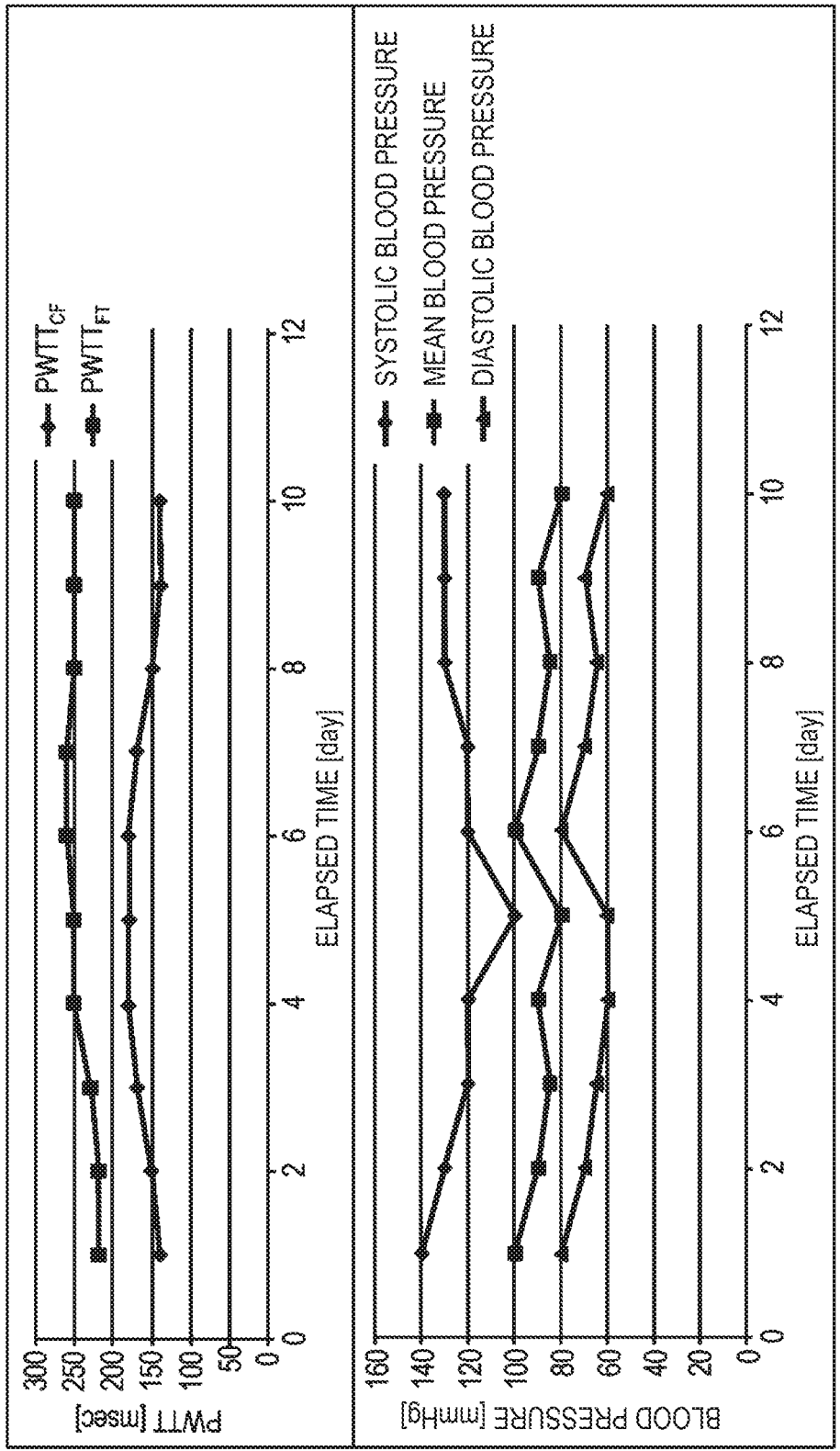
FIG. 7 is a view illustrating an example of a display image in which the $PWTT_{CF}$, the $PWTT_{FT}$ that is calculated from an electrocardiogram and the fingertip pulse wave, and the systolic blood pressure, the diastolic blood pressure, and the mean blood pressure are simultaneously displayed.

FIG. 7 is a view illustrating an example of a display image in which the $PWTT_{CF}$, the $PWTT_{FT}$, and the systolic blood pressure, the diastolic blood pressure, and the mean blood pressure are simultaneously displayed.

The display image of FIG. 7 is configured by two-dimensional graphs of time transitions of the $PWTT_{CF}$, the $PWTT_{FT}$, and time transitions of the systolic blood pressure, the diastolic blood pressure, and the mean blood pressure, and shows changes over time in these values. The abscissa indicates the elapsed time from the timing of hospital discharge of the subject. In the display image, the span and scale of the elapsed time of the abscise are common in the two-dimensional graph of the $PWTT_{CF}$ and the $PWTT_{FT}$, and that of the time transitions of the systolic blood pressure, the diastolic blood pressure, and the mean blood pressure. Therefore, the $PWTT_{CF}$ and the $PWTT_{FT}$, and the systolic blood pressure, the diastolic blood pressure, and the mean blood pressure are displayed in correlation with each other. The blood pressure which is a usual index of circulatory dynamics including the cardiac functions is displayed together with the $PWTT_{CF}$ reflecting the heart contraction function, thereby enabling a sign of heart failure to be early detected.

Although, in the display image shown in FIG. 7, the abscissa indicates the elapsed time from the tuning of hospital discharge of the subject, the abscissa can indicate the acquisition time when the electrocardiogram, the cuff pulse wave, and the fingertip pulse wave are acquired. In this case, the ordinates can indicate the $PWTT_{CF}$ and the $PWTT_{CF}$ which are obtained from the electrocardiogram, cuff pulse wave, and fingertip pulse wave that are acquired from the acquisition time of the abscissa, and the systolic blood pressure, the diastolic blood pressure, and the mean blood pressure. The acquisition time may be additionally indicated at each plot of the two-dimensional graphs shown in FIG. 7.

Figure 8:
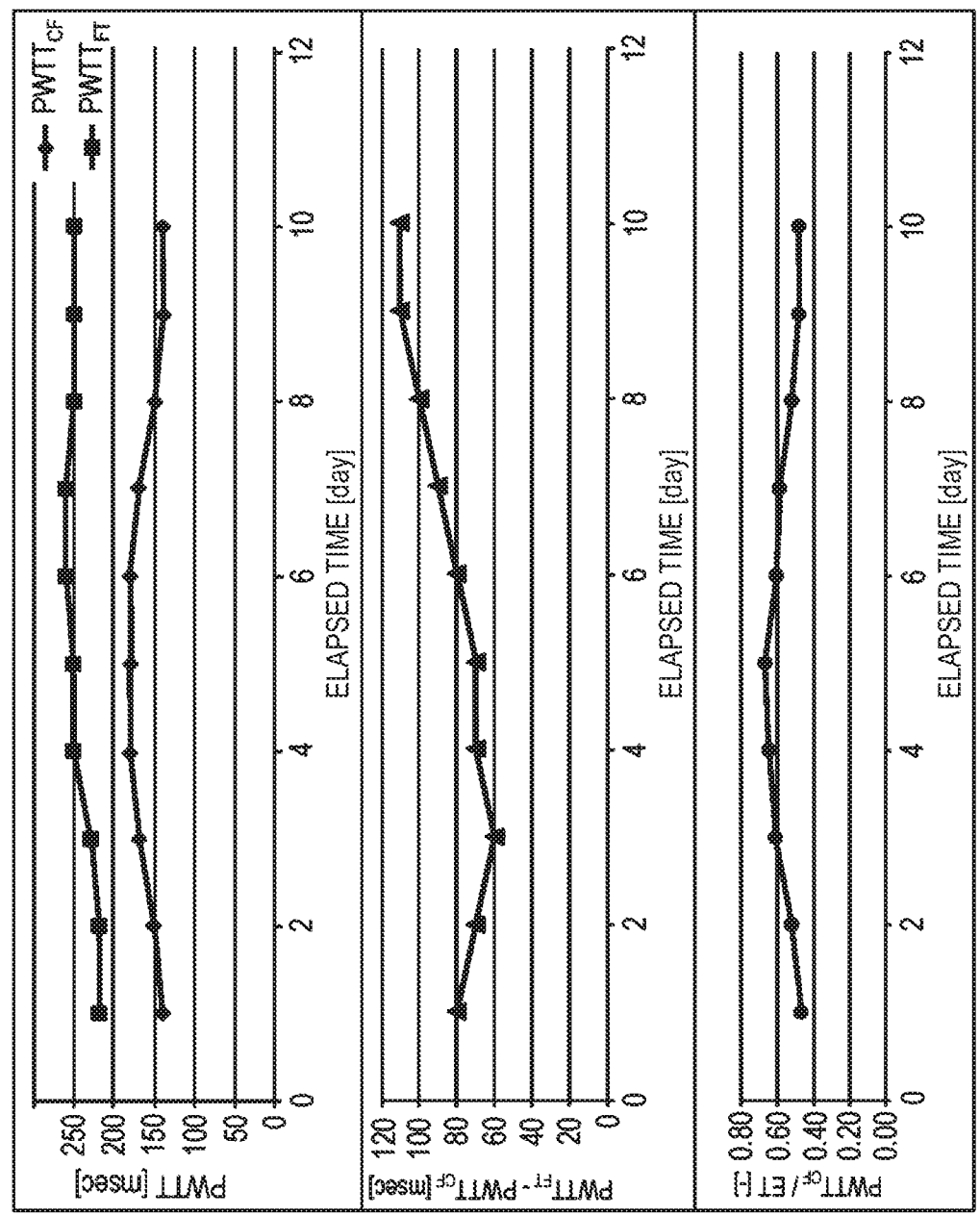
FIG. 8 is a view illustrating an example of a display image in which the $PWTT_{CF}$, the $PWTT_{FT}$, the difference between the $PWTT_{CF}$ and the $PWTT_{FT}$, and a value which is obtained by dividing the $PWTT_{CF}$ by the ejection time ET are simultaneously displayed.

FIG. 8 is a view illustrating an example of a display image in which the $PWTT_{CF}$, the $PWTT_{FT}$, the difference between the $PWTT_{CF}$ and the $PWTT_{FT}$, and the value which is obtained by dividing the $PWTT_{CF}$ by the ET are simultaneously displayed. The display image is configured by two-dimensional graphs of time transitions of the $PWTT_{CF}$, the $PWTT_{FT}$, the difference between the $PWTT_{CF}$ and the $PWTT_{FT}$, and the value which is obtained by dividing the $PWTT_{CF}$ by the ET, and shows changes over time in these values. The abscissa indicates the elapsed time from the timing of hospital discharge of the subject, in the display image, the span and scale of the elapsed time of the abscissa are common in the two-dimensional graph of the $PWTT_{CF}$ and the $PWTT_{FT}$, that of the difference between the $PWTT_{CF}$ and the $PWTT_{FT}$, and that of the value which is obtained by dividing the $PWTT_{CF}$ by the ET. Therefore, the $PWTT_{CF}$ and the $PWTT_{FT}$, the difference between the $PWTT_{CF}$ and the $PWTT_{FT}$, and the value which is obtained by dividing the $PWTT_{CF}$ by the ET are displayed in correlation with one another.

Although, in the display image shown in FIG. 8, the abscissa indicates the elapsed time from the timing of hospital discharge of the subject, the abscissa may indicate the acquisition time when the electrocardiogram, the cuff pulse wave, and the fingertip pulse wave are acquired. In this case, the ordinates can indicate the $PWTT_{CF}$ and the $PWTT_{CF}$ which are obtained from the electrocardiogram, cuff pulse wave, and fingertip pulse wave that are acquired at the acquisition time of the abscissa, the difference between the $PWTT_{CF}$ and the $PWTT_{FT}$, and the value which is obtained by dividing the $PWTT_{CF}$ by the ET. The acquisition time may be additionally indicated at each plot of the two-dimensional graphs shown in FIG. 8.

Figure 9:
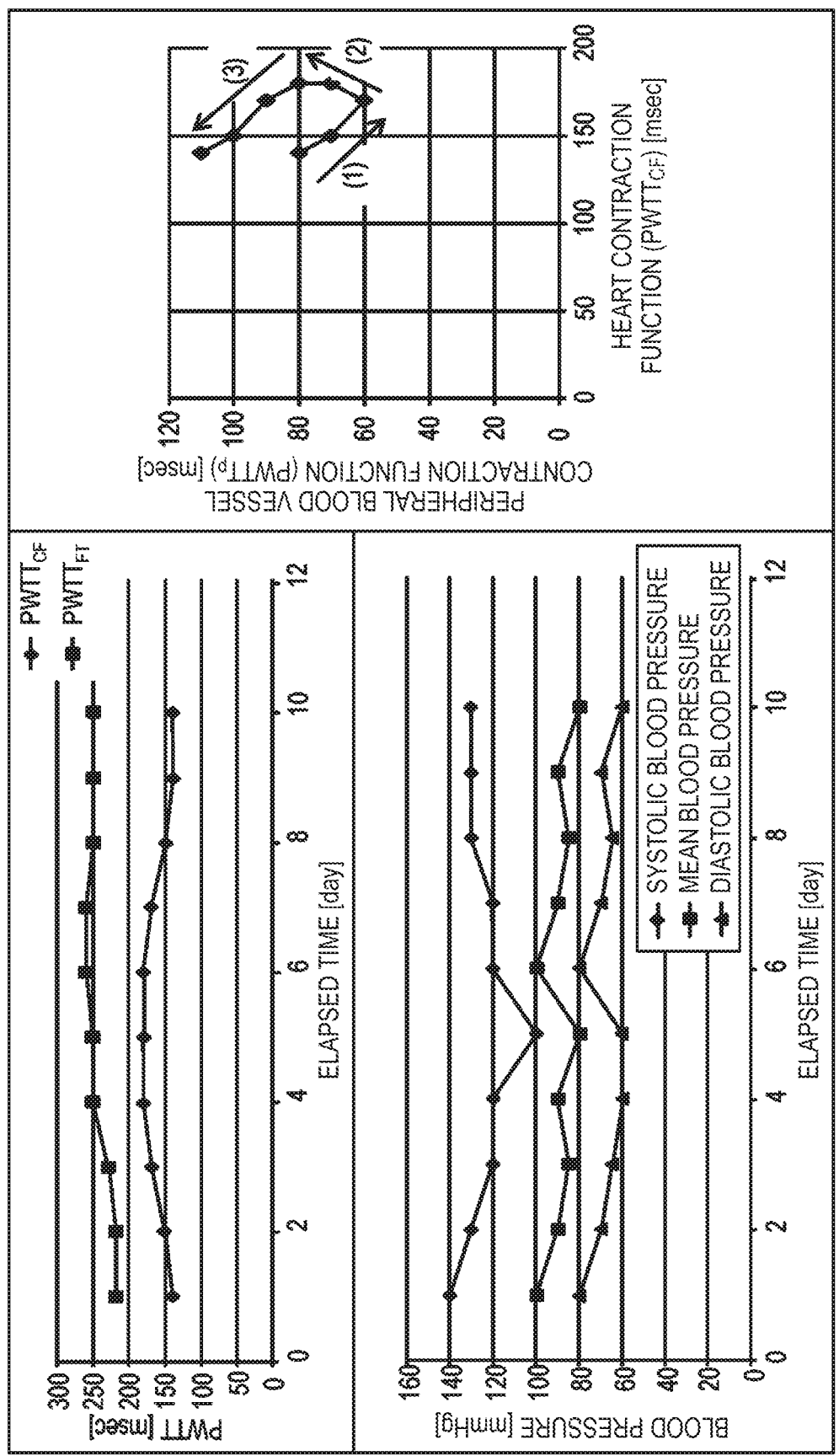
FIG. 9 is a view illustrating an example of a display image in which two-dimensional graphs of: the $PWTT_{CF}$ and the $PWTT_{FT}$; the systolic blood pressure, the diastolic blood pressure, and the mean blood pressure; and the relationship between the $PWTT_{CF}$ and the $PWTT_p$ are simultaneously displayed.

FIG. 9 is a view illustrating an example of a display image in which two-dimensional graphs of relationships between: the $PWTT_{CF}$ and the $PWTT_{FT}$; the systolic blood pressure, the diastolic blood pressure, and the mean blood pressure; and the $PWTT_{CF}$ and the $PWTT_{p}$ (the difference between the $PWTT_{CF}$ and the $PWTT_{FT}$) are simultaneously displayed, in the two-dimensional graph of the relationship between the $PWTT_{CF}$ and the $PWTT_{p}$, the change over time in the relationship between the $PWTT_{CF}$ and the $PWTT_{p}$ is shown by an arrow indicating the direction of the change over time. In the two-dimensional graph, the $PWTT_{CF}$ can be displayed as an index of the heart contraction function, and the $PWTT_{p}$ can be displayed as an index of the peripheral blood vessel contraction function indicating the state of the vascular resistance. According to the two-dimensional graph, if is possible to understand that the heart contraction function and the peripheral blood vessel contraction function track the following changes over time. In the step of (1) of the figure, namely, the heart contraction function is lowered, and the peripheral blood vessel dilates with the result that the blood pressure is lowered. In the step of (2), the heart contraction function is compensated by the contraction of the peripheral blood vessel, and the blood pressure is maintained. In the step of (3), then, the cardiac function is recovered, and the peripheral blood vessel is further contracted, whereby the blood pressure is maintained.

Figure 10:
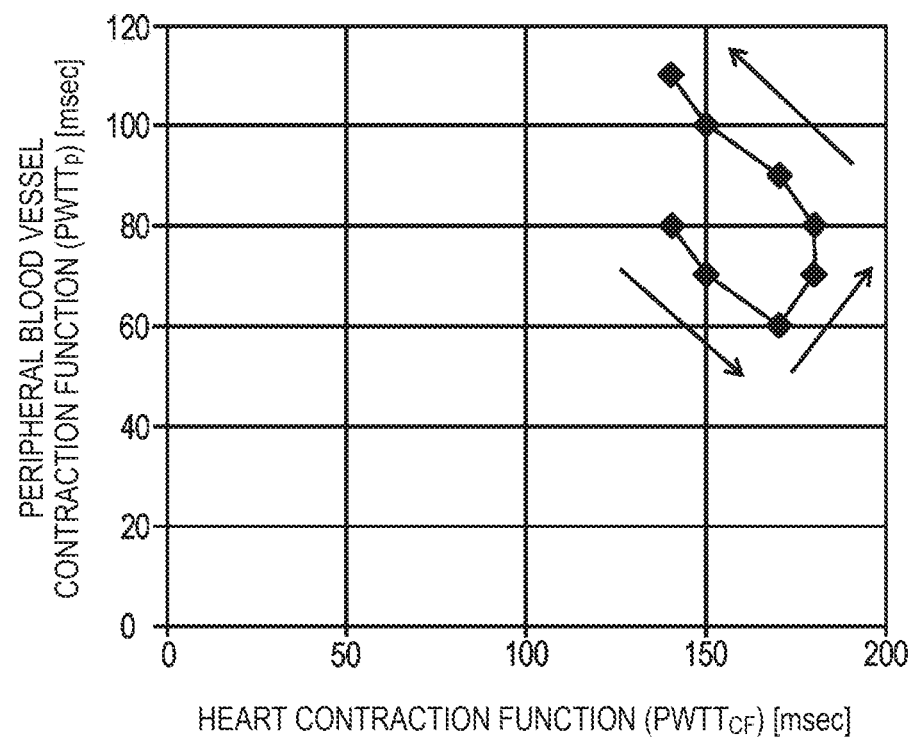
FIG. 10 is a view illustrating an example of a display image of the two-dimensional graph of the relationship between the $PWTT_{CF}$ and the $PWTT_p$.

FIG. 10 is a view illustrating an example of a display image of the two-dimensional graph of the relationship between the $PWTT_{CF}$ and the $PWTT_{p}$. In this way, only the two-dimensional graph of the relationship between the $PWTT_{CF}$ and the $PWTT_{p}$ can be displayed as the display image.

Although, in FIGS. 9 and 10, the $PWTT_{CF}$ is displayed as an index of the heart contraction function, the $PWTT_{CF}$/ET or the average values of the $PWTT_{CF}$ and the $PWTT_{CF}$/ET may be displayed in place of the $PWTT_{CF}$.

The inputting/outputting section 115 is an interface for exchanging signals between the displaying section 120 and the inputting section 130. The inputting/outputting section 115 constitutes the information outputting section and the image outputting section.

The displaying section 120 displays; at least two of the $PWTT_{CF}$, the $PWTT_{FT}$, and the difference between the $PWTT_{CF}$ and the $PWTT_{FT}$; the value which is obtained by dividing the $PWTT_{CF}$ by the ET; the blood pressure; and the display image. These sets of information are received from the controller 110.

The inputting section 130 receives various inputs.

Figure 11:
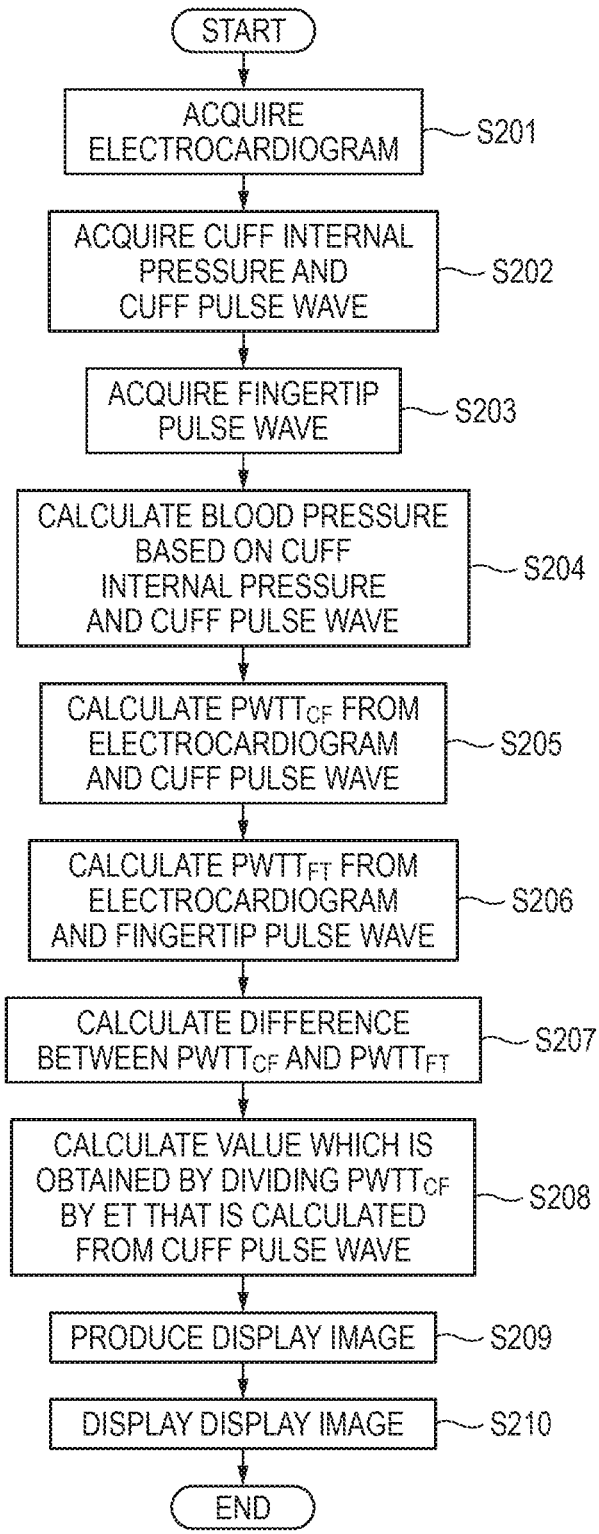
FIG. 11 is a flowchart illustrating the operation of a circulatory dynamic measuring apparatus.

FIG. 11 is a flowchart illustrating the operation of the circulatory dynamic measuring apparatus. The flowchart can be executed by the CPU 111 in accordance with the circulatory dynamic measuring program P.

The CPU 111 acquires the electrocardiogram of the subject from the electrocardiogram measuring apparatus 200 (S201).

The CPU 111 acquires the cuff internal pressure and the cuff pulse wave from the blood pressure measuring apparatus 300 (S202).

The CPU 111 acquires the fingertip pulse wave from the photoelectric sensor 400 (S203).

The CPU 111 calculates the blood pressure based on the cuff internal pressure and the cuff pulse wave (S204).

The CPU 111 calculates the $PWTT_{CF}$ from the electrocardiogram and the cuff pulse wave (S205), and further calculates the $PWTT_{FT}$ from the eleclrocardiogram and the fingertip pulse wave (S206).

The CPU 111 calculates the difference between the $PWTT_{CF}$ and the $PWTT_{FT}$ (S207).

The CPU 111 calculates the value which is obtained by dividing the $PWTT_{CF}$ by the ET that is calculated from the cuff pulse wave (S208).

The CPU 111 produces a display image in which the $PWTT_{CF}$, the $PWTT_{FT}$, the difference between the $PWTT_{CF}$ and the $PWTT_{FT}$, the value which is obtained by dividing the $PWTT_{CF}$ by the ET, and the blood pressure are simultaneously displayed (S209).

The CPU 111 transmits the display image to the displaying section 120 to cause the image to be displayed thereon (S210).

The embodiment attains the following effects.

The first pulse wave transmit time is calculated from the electrocardiogram of the subject and the pulse wave of the first portion, and the second pulse wave transmit time is calculated from the electrocardiogram and the second pulse wave of the second portion that is different from the first portion. Therefore, the pulse wave propagation in the portion which is proximal to the heart, and that in the portion which is distal Horn the heart can be compared to each other, whereby the state of the heart contraction function of the subject, and that of the vascular resistance are enabled to be simultaneously known.

Moreover, the upper arm of the subject is set as the first portion, and the fingertip is set as the second portion. Therefore, the state of the heart contraction function of the subject, and that of the vascular resistance can be easily known.

Moreover, the difference between the first and second pulse wave transmit times is calculated. Therefore, the state of the vascular resistance of the subject can be clearly known.

Moreover, a two-dimensional graph of the relationship of at least two of the first pulse wave transmit time, the second pulse wave transmit time, and the difference between the first and second pulse wave transmit times is calculated, and a display image in which the two-dimensional graph is displayed is produced. Therefore, a change in the mutual relationship between the state of the heart contraction function of the subject, and that of the vascular resistance can be easily known, and it is possible to adequately determine whether there is a sign of heart failure or not.

Moreover, a display image in which at least two of the first pulse wave transmit time, the second pulse wave transmit time, and the difference between the first, and second pulse wave transmit times are simultaneously displayed is produced. Therefore, the states of the heart contraction function and vascular resistance of the subject can be simultaneously known from the image.

Moreover a display image is produced in which at least two of the first pulse wave transmit time, the second pulse wave transmit time, and the difference between the first and second pulse wave transmit times are displayed together with the acquisition time when the electrocardiogram, first pulse wave, and second pulse wave which are used for calculating these values are acquired. Therefore, the date and time when the information indicating the states of the heart contraction function and vascular resistance of the subject can be easily known.

Moreover two-dimensional graphs in which the acquisition time is set as the abscissa, and at least two of the first and second pulse wave transmit times that are calculated based on the electrocardiogram, first pulse wave, and second pulse wave that are acquired at the acquisition time, and the difference between these values are set as the ordinates are produced as the display image. Therefore, the change over time in the information indicating the states of the heart contraction function of the subject and the vascular resistance can be clearly known as time transition.

Moreover, the blood pressure is calculated based on the first pulse wave, and a display image in which at least two of the first and second pulse wave transmit times that are correlated with the calculated blood pressure, and the difference between these values are displayed is produced. Therefore, the image from which the states of the heart contraction function and the vascular resistance can be known, and the blood pressure which is a usual index of circulatory dynamics are simultaneously displayed in correlation with one another, thereby enabling a sign of heart failure to be detected accurately and early.

Moreover, the apparatus has the information outputting section which outputs at least two of the first pulse wave transmit time, the second pulse wave transmit time, and the difference between the first pulse wave transmit time and the second pulse wave transmit time. Therefore, at least two of the first pulse wave transmit time, the second pulse wave transmit time, and the difference between the first pulse wave transmit time and the second pulse wave transmit time can be transmitted as data.

Moreover, the apparatus has the image outputting section which outputs the above-described display image. Therefore, the display image can be transmitted as data.

Although the circulatory dynamic measuring apparatus, circulatory dynamic measuring method, and circulatory dynamic measuring program of the embodiments of the presently disclosed subject matter have been described, the invention is not limited to the above-described embodiments.

For examples, the pulse wave, which, in the above-described embodiments is measured by using the cuff may be measured by an impedance plethysmograph.

The circulatory dynamic measuring apparatus may be configured by only the controller. In this case, the displaying section and the inputting section can be configured as external devices which are connected to the circulatory dynamic measuring apparatus, respectively.

A part or all of the functions which are to be executed by programs in the embodiments may be executed by hardware such as electronic circuits.

The circulatory dynamic measuring program P may be downloaded through a network such as the internet or may be recorded in a non-transitory computer-readable recording medium. Examples of such a computer-readable recording medium include an optical medium such as a CD-ROM (Compact Disc-ROM), a magnetic recording medium such as a memory card.

According to the presently disclosed subject matter, there is also provided a circulatory dynamic measuring apparatus comprising: an electrocardiogram acquiring section which is configured to acquire an electrocardiogram of a subject; a first pulse wave acquiring section which is configured to acquire a first pulse wave in a first portion of the subject; a second pulse wave acquiring section which is configured to acquire a second pulse wave in a second portion of the subject, the second portion being different from the first portion; a first calculator which is configured to calculate a first pulse wave transmit time from the electrocardiogram and the first pulse wave; and a second calculator which is configured to calculate a second pulse wave transmit time from the electrocardiogram and the second pulse wave.

The first portion is an upper arm of the subject, and the first pulse wave acquiring section is configured to acquire a pulse wave in the upper arm of the subject, as the first pulse wave, and the second portion is a fingertip of the subject and the second pulse wave acquiring section is configured, to acquire a fingertip poise wave in the fingertip of the subject, as the second pulse wave.

The circulatory dynamic measuring apparatus further comprises: a third calculator winch is configured to calculate a difference between the first pulse wave transmit time and the second pulse wave transmit time.

The circulatory dynamic measuring apparatus further comprises: a fourth calculator which is configured to calculate a two-dimensional graph of a relationship of at least two of: the first pulse wave transmit time; the second pulse wave transmit time; and the difference between the first pulse wave transmit time and the second pulse wave transmit time; and a display image producing section which is configured to produce a display image in which the two-dimensional graph is displayed.

The circulatory dynamic measuring apparatus further comprises a display image producing section which is configured to produce a display image in which at least two of the first pulse wave transmit time; the second pulse wave transmit time; and the difference between the first pulse wave transmit time and the second pulse wave transmit time are displayed.

The display image producing section is configured to produce a display image in which an acquisition time when the electrocardiogram, the first pulse wave, and the second pulse wave are acquired is displayed together with at least two of: the first pulse wave transmit time which is calculated from the electrocardiogram and the first pulse wave that are acquired at the acquisition time; the second pulse wave transmit time which is calculated from the electrocardiogram and the second pulse wave that are acquired at the acquisition time; and the difference between the first pulse wave transmit time which is calculated from the electrocardiogram and the first pulse wave that are acquired at the acquisition time, and the second pulse wave transmit time which is calculated front the electrocardiogram and the second pulse wave that are acquired at the acquisition time.

The display image producing section is configured to produce a display image in which at least two of the first pulse wave transmit time; the second pulse wave transmit time; and the difference between the first pulse wave transom time and the second pulse wave transmit tune are displayed in a form of two-dimensional graphs in which the acquisition time is set as an abscissa, and at least two of: the first pulse wave transmit time which is calculated from the electrocardiogram and the first pulse wave that are acquired at the acquisition time of the abscissa; the second pulse wave transmit time which is calculated from the electrocardiogram and the second pulse wave that are acquired at the acquisition time of the abscissa; and the difference between the first pulse wave transmit time which is calculated from the electrocardiogram and the first pulse wave that are acquired at the acquisition time of the abscissa, and the second pulse wave transmit time which is calculated from the electrocardiogram and the second pulse wave that are acquired at the acquisition time of the abscissa are set as ordinates.

The circulatory dynamic measuring apparatus further comprises: a blood pressure blood pressure calculator which is configured to calculate a blood pressure based on the first pulse wave, and the display image producing section is configured to produce the display image in which at least two of: the first pulse wave transmit time; the second pulse wave transmit time; and the difference between the first pulse wave transmit time and the second pulse wave transmit time, and the calculated blood pressure are displayed in correlation with one another.

The circulatory dynamic measuring apparatus further comprises: an information outputting section which is configured to output at least two of: the first pulse wave transmit time; the second pulse wave transmit time; and the difference between the first pulse wave transmit time and the second pulse wave transmit time.

The circulatory dynamic measuring apparatus further comprises: an image outputting section winch is configured to output the display image.

What is claimed is:

1. A circulatory dynamic measuring apparatus comprising:
   at least one processor configured to:
   acquire an electrocardiogram of a subject;
   acquire a pulse wave of an upper arm of the subject when a pressure applied to the upper arm by a cuff attached to the upper arm of the subject is equal to or greater than an atmospheric pressure, the pulse wave being superimposed on an internal pressure of the cuff;
   calculate a pulse wave transmit time from the electrocardiogram and pulse wave, the pulse wave transmit time being a sum of a time period from an R wave in the electrocardiogram to a start of a rising of an aortic root blood pressure and a time period for the pulse wave to reach the upper arm from the subject's heart through an artery;
   calculate a time period from a start of a rising of the pulse wave to a notch;
   calculate a contraction function of a ventricle of the subject by dividing the calculated pulse wave transmit time by the time period from the start of a rising of the pulse wave to the notch;
   calculate a blood pressure based on the pulse wave; and
   produce a display image on a display in which:
   an acquisition time when the electrocardiogram and the pulse wave are acquired is displayed together with the contraction function of the ventricle of the subject; and
   the blood pressure and the contraction function of the ventricle of the subject are displayed in synchronization.

2. The circulatory dynamic measuring apparatus according to claim 1, wherein the processor is configured to acquire the pulse wave during a process of changing a cuff pressure which is applied to the upper arm by the cuff attached to the upper arm of the subject, in order to measure a blood pressure.

3. The circulatory dynamic measuring apparatus according to claim 1, wherein the processor is configured to produce the display image further in which the contraction function of the ventricle of the subject is displayed in a form of a two-dimensional graph in which the acquisition time is an abscissa of the two-dimensional graph, and the contraction function of the ventricle of the subject and that is based on the pulse wave transmit time obtained from the electrocardiogram and the pulse wave that are acquired at the acquisition time of the abscissa is an ordinate of the two-dimensional graph.

4. The circulatory dynamic measuring apparatus according to claim 1, further comprising: the display configured to output the blood pressure and the contraction function of the ventricle of the subject.

5. The circulatory dynamic measuring apparatus according to claim 1, further comprising: the display configured to output the display image.

6. The circulatory dynamic measuring apparatus according to claim 1, wherein the at least one processor is further configured to:
   identify the R wave in the electrocardiogram; and
   identify a start point of a rising of the pulse wave of the upper arm based on the acquired pulse wave,
   wherein the pulse wave transmit time is calculated as a time period from the identified R wave in the electrocardiogram to the identified start point of the rising of the pulse wave of the upper arm.

7. A circulatory dynamic measuring method comprising:
   acquiring an electrocardiogram of a subject;
   acquiring a pulse wave of an upper arm of the subject when a pressure applied to the upper arm by a cuff attached to the upper arm of the subject is equal to or greater than an atmospheric pressure, the pulse wave being superimposed on an internal pressure of the cuff;
   calculating a pulse wave transmit time from the electrocardiogram and pulse wave, the pulse wave transmit time being a sum of a time period from an R wave in the electrocardiogram to a start of a rising of an aortic root blood pressure and a time period for the pulse wave to reach the upper arm from the subject's heart through an artery;
   calculating a time period from a start of a rising of the pulse wave to a notch;
   calculating a contraction function of a ventricle of the subject by dividing the calculated pulse wave transmit time by the time period from the start of a rising of the pulse wave to the notch;
   calculating a blood pressure based on the pulse wave; and
   displaying an image on a display in which:
      an acquisition time when the electrocardiogram and the pulse wave are acquired is displayed together with the contraction function of the ventricle of the subject; and
      the blood pressure and the contraction function of the ventricle of the subject are in synchronization.

8. A non-transitory computer-readable recording medium in which a program causing a computer to execute the circulatory dynamic measuring method according to claim 7 is recorded.

9. A circulatory dynamic measuring method comprising:
   acquiring an electrocardiogram of a subject;
   acquiring a first pulse wave in a first portion of the subject when a pressure applied to the first portion by a cuff attached to the first portion of the subject is equal to or greater than an atmospheric pressure, the pulse wave being superimposed on an internal pressure of the cuff;
   acquiring a second pulse wave in a second portion of the subject, the second portion being different from the first portion;
   calculating a first pulse wave transmit time from the electrocardiogram and the first pulse wave which are acquired, the first pulse wave transmit time being a sum of a time period from an R wave in the electrocardiogram to a start of a rising of an aortic root blood pressure and a time period for the first pulse wave to reach the first portion of the subject from the subject's heart through an artery;
   calculating a second pulse wave transmit time from the electrocardiogram and the second pulse wave which are acquired;
   calculating a time period from a start of a rising of the first pulse wave to a notch;
   calculating a contraction function of a ventricle of the subject by dividing the calculated pulse wave transmit time by the time period from the start of a rising of the pulse wave to the notch;
   calculating a blood pressure based on the first pulse wave; and
   displaying an image on a display in which:
      an acquisition time when the electrocardiogram, the first pulse wave, and the second pulse wave are acquired, are displayed together with the contraction function of the ventricle of the subject; and
      the blood pressure and the contraction function of the ventricle of the subject are in synchronization.

10. A non-transitory computer-readable recording medium in which a program causing a computer to execute the circulatory dynamic measuring method according to claim 9 is recorded.

11. The circulatory dynamic measuring method according to claim 9, further comprising displaying the first pulse wave transmit time, the second pulse wave transmit time, and the difference between the first pulse wave transmit time and the second pulse wave transmit time in synchronization.

* * * * *

UNITED STATES PATENT AND TRADEMARK OFFICE
CERTIFICATE OF CORRECTION

PATENT NO. : 11,974,839 B2
APPLICATION NO. : 15/923040
DATED : May 7, 2024
INVENTOR(S) : Teiji Ukawa It is certified that error appears in the above-identified patent and that said Letters Patent is hereby corrected as shown below:

On the Title Page

Item (57); Line 4, "to acquire a poise" should read -- to acquire a pulse --

In the Specification

Column 4, Line 55, "referred to as 'PWTTs')." should read -- referred to as 'PWTTa'). --

Column 10, Line 2, "cuff is attached, through" should read -- cuff 310 is attached, through --

Column 10, Line 56, "by the EX." should read -- by the ET. --

Signed and Sealed this
Twelfth Day of November, 2024

Katherine Kelly Vidal
*Director of the United States Patent and Trademark Office*